(12) United States Patent
Heiter-Kelly

(10) Patent No.: US 9,821,137 B2
(45) Date of Patent: Nov. 21, 2017

(54) HARMONIOUS SCALE INSTRUMENT

(76) Inventor: Carla Rose Heiter-Kelly, London (CA)

( * ) Notice: Subject to any disclaimer, the term of this patent is extended or adjusted under 35 U.S.C. 154(b) by 84 days.

(21) Appl. No.: 13/825,202

(22) PCT Filed: Sep. 20, 2011

(86) PCT No.: PCT/CA2011/001053
§ 371 (c)(1),
(2), (4) Date: Mar. 20, 2013

(87) PCT Pub. No.: WO2012/037653
PCT Pub. Date: Mar. 29, 2012

(65) Prior Publication Data
US 2013/0178695 A1    Jul. 11, 2013

Related U.S. Application Data

(60) Provisional application No. 61/434,119, filed on Jan. 19, 2011.

(51) Int. Cl.
*A61M 21/02*      (2006.01)
*A61N 1/36*       (2006.01)
(Continued)

(52) U.S. Cl.
CPC ......... *A61M 21/02* (2013.01); *A61N 1/36025* (2013.01); *G09B 15/02* (2013.01);
(Continued)

(58) Field of Classification Search
CPC .......... G10H 7/00; G10H 1/26; A61M 21/00; A61M 2021/0027; A61M 2021/0044; A61M 2021/0055; A61M 2021/0066
(Continued)

(56) References Cited

U.S. PATENT DOCUMENTS 2,263,106 A * 11/1941 Sebouh ................ G10D 13/085
                                                116/DIG. 30
3,447,411 A *  6/1969 Bloxsom, Jr. ................... 84/264
(Continued)

FOREIGN PATENT DOCUMENTS

JP          5323958 A     12/1993

OTHER PUBLICATIONS

"The Ancient Solfeggio Scale", downloaded from http://atunedvibrations.com, Jan. 12, 2015, five pages.*
(Continued)

*Primary Examiner* — Samuel Gilbert
(74) *Attorney, Agent, or Firm* — Eduardo Krupnik

(57) ABSTRACT

The present invention relates to a musical instrument for producing a harmonious scale of musical notes. The instrument includes nine separate sound actuators each of which is configured to cause the musical instrument to generate a different frequency selected from the group of frequencies comprising 174 Hz, 285 Hz, 396 Hz, 417 Hz, 528 Hz, 639 Hz, 741 Hz, 852 Hz and 963 Hz, the musical instrument being configured such that physically manipulating the sound actuators causes the musical instrument to generate the frequency corresponding to the sound actuator manipulated. The invention is also directed at a system for—writing music to be played with a musical instrument incorporating the harmonious scale of musical notes as described above. The notation system includes a staff of five parallel and horizontal lines separated by four spaces, the first line indicating a first note of 174 Hz, the space immediately above the first line indicating a second note of 285 Hz, the second line indicating a third note of 396 Hz, the space immediately above the second line indicating a fourth note of 417 Hz, the third line indicating a fifth note of 528 Hz, the space immediately above the third line indicating a sixth
(Continued)

note of 639 Hz, the fourth line indicating a seventh note of 741 Hz, the space immediately above the fourth line indicating an eighth of 852 Hz and the fifth line, indicating a ninth note of 963 Hz.

12 Claims, 4 Drawing Sheets

(51) Int. Cl.
      *G10D 1/00*       (2006.01)
      *G10G 1/00*       (2006.01)
      *G09B 15/02*      (2006.01)
      *G09B 15/06*      (2006.01)

(52) U.S. Cl.
      CPC ............... *G09B 15/06* (2013.01); *G10D 1/00* (2013.01); *G10G 1/00* (2013.01)

(58) Field of Classification Search
      USPC ..................................................... 600/26–28
      See application file for complete search history.

(56) References Cited

U.S. PATENT DOCUMENTS

| | | | | |
|---|---|---|---|---|
| 3,773,049 | A | * | 11/1973 | Rabichev et al. ................. 607/1 |
| 3,878,750 | A | * | 4/1975 | Kapps ............................. 84/609 |
| 5,175,387 | A | * | 12/1992 | Greory ............................ 84/267 |
| 5,986,194 | A | * | 11/1999 | Schwartz et al. ............... 84/404 |
| 6,656,137 | B1 | * | 12/2003 | Tyldsley et al. ................ 601/15 |
| 2004/0187673 | A1 | * | 9/2004 | Stevenson ...................... 84/737 |
| 2006/0281543 | A1 | * | 12/2006 | Sutton et al. ................... 463/29 |

OTHER PUBLICATIONS

All Solfeggio Hz Chakra Tune, Jezebel Decibel, Jun. 25, 2008, 4 pages.*
Johnathan Goldman, Holy Harmony "Solfeggio Tuning Forks", Sep. 5, 2010, 1 page, from the internet archive, Wayback machine.*
Grout, Donald Jay, A History of Western Music, 3rd edition, 1980, p. 2-11, W. W. Norton and Company, Inc.
Horowitz, Leonard G. and Puleo, Joseph, Heating Codes for the Biological Apocalypse, 2007, p. 52-57, Tetrahedron Publishing Group.
Melchizedek, Drunvalo, The Ancient Secret of the Flower of Life, 2000, vol. 2, p. 244, Light Technology Publishing.
Walton et al. A preliminary study with implications for bioenergetic healing, The Journal of Hydrocreationism, Jan. 2009, p. 1-38, vol. 1, No. 1.
Definition of Music, www.dictionary.com/browse/music, Mar. 16, 2016, p. 1-5.
Norman-Haignere, Sam et al, Distinct Cortical Pathways for Music and Speech Revealed by Hypothesis-Free Voxel Decomposition, Neuron, Dec. 16, 2105, vol. 88, Issue 6, p. 1281-1296, Elsevier Inc.
Mowry, Life Transformational Tools #9: The Ancient Solfeggio Frequencies—The Perfect Circle of Sound Part 3, http://www.miraclesandinspiration.com/solfeggiofrequencies3.html, 2009.
Kelley, Carla Rose, The Sacred Scale: More Effective Than Drugs, 2nd Biennial Conference of the Interdisciplinary Society for Quantitative Research in Music and Medicine, Jrnl of Inter. Soc. for Res. in Music and Medicine, Jul. 2013, p. 80-95.

* cited by examiner

HARMONIOUS SCALE INSTRUMENT

CROSS REFERENCE TO RELATED APPLICATIONS

This application is a national stage application under 35 U.S.C. 371 of International Application No. PCT/CA2011/001053, filed Sep. 20, 2011, which in turn claims the benefit under 35 U.S.C. 119(e) of U.S. patent application No. 12/885,863, filed Sep. 20, 2010, and from U.S. Provisional Application Ser. No. 61/434,119, filed Jan. 19, 2011, the contents of each of which are hereby incorporated by reference into the present disclosure.

FIELD OF THE INVENTION

The invention relates generally to instruments for generating musical notes, to notation systems for writing music, and to teaching and therapeutic methods comprising the use of said instruments.

BACKGROUND OF THE INVENTION

Earliest historical records demonstrate that music was an inseparable part of religious ceremonies. Plato and Pythagoras taught the world to understand that the whole spiritual and physical universe was the understanding of numbers. So the system of music, sounds, and rhythms, being ordered by numbers, was conceived as exemplifying the harmony of the cosmos and corresponding to it. The most important aspects of Greek thoughts on music is "that there is a power in music akin to the power of words for influencing human thought and action and that therefore an artist, whether in music or words, is under obligation to exercise use of this power with due respect for its effect on others. Music or vibration could heal sickness, purify the body and mind and work miracles in the realm of nature" (History of Western Music, 3rd ed. Donald Jay Grout, pg 2-11). Similar powers attributed to music may also be found in the Old Testament: David cures Saul's madness by playing the harp (I. Samuel XVI: 14-23) or of the trumpet blasts and shouting that toppled the walls of Jericho (Joshua VI: 12-20).

The great composers of the Baroque, Classical and Romantic eras tuned their instruments through their own genius ear in what resonated with nature. In 1919 it was decided to standardize the tuning system of Western music so that all instruments could play together. This 12 tone Equal Temperament System based on man-made standards in which A was equal to 440 Hz has continued to the present time.

If our present diatonic scale is not in harmony with mankind or nature, then it would be imperative to create a system that is. Dissonant and unharmonious vibrations or sounds may create anxiety, tension, health problems, mental disorders, emotional disorders, and a feeling of disconnectedness to the universe.

The present diatonic system of Western music is a tonal system in which specific notes such as the tonic, dominant and leading notes have more importance than the other notes. However, the dominant-seventh chord is the most "unstable" chord in music writing and demands resolution to the tonic.

In terms of music, "harmony" may be described as the sound of two or more notes heard simultaneously, to produce chords, and their successive use to produce chord progressions. The term may not be disassociated with the rhythmic aspects of music. For example, the use of dissonance and consonance creates tensions generating a powerful forward momentum. Harmony may also provide punctuation marks in the form of cadences, simple readily recognizable chord progressions that mark a natural end to a phrase in a stereotyped way.

Harmony may be more developed in Western music than in any other region. Different eras of Western music have held different ideas as to what kinds of harmony are acceptable or good. For example:

1. In the Middle Ages (450-1450), the concept of harmony concerned combinations of two notes, open 5ths and octaves.
2. In Medieval and early Renaissance (1450's) music, even a full major triad was felt inappropriate for the last chord of a piece which normally would embody the final note (in more than one octave) and the 5th above it.
3. In the Renaissance (1450-1600), three-note harmony became the norm and the triad had become the main unit of harmony. This remained the basic element in Western harmony until the 20th Century, even when harmony was composed in four parts or more.
4. From the beginning of the Baroque era (c1600) harmony was widely understood as the chords with which a melody was accompanied (basso continuo or figured bass).
5. From the 1600-1900's full triads were usual for concluding chords. Harmony was sometimes seen as the "opposite" of counterpoint, because it primarily operates vertically, whereas counterpoint seemed to operate horizontally. The two were not opposed: most contrapuntal writing, especially in the 1600-1900 period, was governed by harmonic progression while, equally, harmony was concerned with the movement of individual voices.
6. In the 19th Century, there was much more chromatic alteration of notes being used, particularly by Wagner.
7. In the 20th Century, composers treated dissonance more freely and felt it was unnecessary to resolve chords, which in earlier eras would have been considered dissonant. The principles of triadic harmony were under attack from Bartok who, inspired by the folk music from which he came, was constructing chords based on the interval of a 4th. Schoenberg used first atonal and then 12 note methods of composition. Stravinsky composed predominantly tonal music and left dissonances unresolved to tease the ear. There was the birth of a "world music" culture.
8. In the 21st Century, there may be a desire to recapture music's original purpose of divination and to restore the Sacredness back into the musical world. There may be also growing awareness that we are not tuning our instruments in "harmony" with the "ALL".

As such, another definition of "harmony" surges, which may be described as a satisfying arrangement marked by even distribution of elements, as in design, proportion, and symmetry.

For the general populations to hear more harmonious sounds may be beneficial on all levels of being. A more harmonious, atonal system may open up a new category of study of music for the "seasoned" musicians, a less complicated study with a focus on creating and healing (and not on performance), and may allow people who would not otherwise play musical instruments to have this option.

Music has always been a reflection of the culture that gave rise to it and a reflection of what was going on in the world, politically, socially, and philosophically. Playing atonal, modal music, in which all tones are in harmony with each other and with nature, may reflect and enhance the move of the world towards unity, with less division among races, nations and peace and harmony among all, as well as living intentionally knowing that we are all affected and affect each other by the sounds around us. Therefore, an improved harmonious musical device would be beneficial.

Sacred Geometry can be defined as an ancient science that explains the energy patterns behind creation and the unification of all things. On every scale, every natural pattern of growth or movement conforms inevitably to one or more geometric shapes. Although it is found within the entire universe, the more obvious can be seen in snakeskin, flower petals, DNA, cornea of our eye, a nautilus shell, snowflakes, and so forth.

Sacred Geometry may also be defined as the relationship between number, proportion, astronomy and music and it is so harmoniously proportionate, thus constructed in the most beautiful method, people travel great distances to admire it. Examples of Sacred Geometry in architecture can be seen in the Egyptian pyramids, or the great Cathedrals, or the Parthenon, Acropolis, Athens that fits almost precisely into a golden rectangle. The Fibonnaci Series is part of the Sacred Geometry. If one divides any number in the Fibonacci sequence by the one before it, the result approaches the number phi ($\phi$) 1.61803 . . . . For example 55/34, or 21/13. This ratio is known as the Golden Ratio.

Today, architects, and artists proportion their work to approximate the Golden Ratio, especially in the form of the golden rectangle, in which the ratio of the longer side to the shorter is the golden ratio, believing this proportion to be aesthetically most pleasing.

Modern medicine presently uses frequency devices and technology which include many frequencies, and complicated procedures for healing and diagnostic purposes. Research into a more complete system of healing frequencies may not only simplify, and enhance the present technology, but also the recovery or prevention of disease may change profoundly.

Therefore, what is needed is a new harmonious system which would involve creating a new category of musical instruments or devices tuned with a new harmonious scale. What is also needed is a new set of instruments which incorporate the sacred geometry. Harmonious vibrations may serve to create feelings of peace, love, harmony, health and wellness amongst humans, animals and nature.

SUMMARY OF THE INVENTION

In accordance with one embodiment of the present invention, there is provided a musical instrument, said instrument comprising nine separate sound actuators each of which configured to cause the musical instrument to generate a different frequency selected from the group of frequencies comprising 174 Hz, 285 Hz, 396 Hz, 417 Hz, 528 Hz, 639 Hz, 741 Hz, 852 Hz and 963 Hz, the musical instrument being configured such that physically manipulating the sound actuators causes the musical instrument to generate the frequency corresponding to the sound actuator manipulated. In aspects, the musical instruments of the present invention, in either acoustic or electronic devices, may be used in methods for healing, teaching, or in methods for creating music.

In accordance with another embodiment of the present invention, there is provided a musical instrument for producing a scale of musical notes, the musical instrument consisting of nine strings coupled to a resonator. Each of the strings is mounted to the musical instrument such that each of the strings can vibrate at a specific frequency when manipulated by a user, the first string being configured to vibrate at a frequency of 963 Hz, the second string being configured to vibrate at 852 Hz, the third string being configured to vibrate at 741 Hz, the fourth string being configured to vibrate at 639 Hz, the fifth string being configured to vibrate at 528 Hz, the sixth string being configured to vibrate at 417 Hz, the seventh string being configured to vibrate at 396 Hz, the eighth string being configured to vibrate at 285 Hz and the ninth string being configured to vibrate at 174 Hz.

In accordance with another embodiment of the present invention, there is provided a musical instrument for producing a scale of musical notes, said musical instrument consisting of nine strings of different lengths coupled to a resonator. The ninth, eighth, and seventh strings each having a gauge of 0.02, the sixth, fifth and fourth strings each having a gauge of 0.018, the third string having a gauge of 0.015, the second string having a gauge of 0.014 and the first string having a gauge of 0.012, the strings each being tensioned such that the first string vibrates at 963 Hz, the second string vibrates at 852 Hz, the third string vibrates at 741 Hz, the fourth string vibrates at 639 Hz, the fifth string vibrates at 528 Hz, the sixth string vibrates at 417 Hz, the seventh string vibrates at 396 Hz, the eighth string vibrates at 285 Hz and the ninth string vibrates at 174 Hz.

In aspects, the musical instruments of the present invention are either electronic or acoustical.

In accordance with yet another embodiment of the present invention there is provided a notation system for writing music having a series of different harmonious notes. The notation system comprises marking the different notes to be played on a staff of five parallel and horizontal lines separated by four spaces, the first line being the lowermost line indicating a first note with a frequency of 174 Hz, the space immediately above the first line indicating a second note with a frequency of 285 Hz, the second line indicating a third note with a frequency of 396 Hz, the space immediately above the second line indicating a fourth note with a frequency of 417 Hz, the third line indicating a fifth note with a frequency of 528 Hz, the space immediately above the third line indicating a sixth note with a frequency of 639 Hz, the fourth line indicating a seventh note with a frequency of 741 Hz, the space immediately above the fourth line indicating an eighth note with a frequency of 852 Hz and the fifth line, being the topmost line, indicating a ninth note with a frequency of 963 Hz.

In accordance with yet another embodiment of the present invention there is provided a method of treating a person using any of the musical instruments of the present invention, the method including the steps of playing a series of the musical notes while the person listens to the series of musical notes.

In accordance with another embodiment of the invention there is provided a method for treating a disorder comprising exposing a subject to one or more frequencies produced by a musical instrument, said one or more frequencies selected from the group of frequencies comprising 174 Hz, 285 Hz, 396 Hz, 417 Hz, 528 Hz, 639 Hz, 741 Hz, 852 Hz and 963 Hz. In aspects, the frequencies are selected relative to a target tissue of the subject. In aspects the disorders are selected from the group consisting of selected from physiological, neurological, behavioural and spiritual disorders.

In another aspect, the present invention provides for a method for practicing sound healing, said method comprising exposing a subject to frequencies produced by a musical instrument for a time effective to produce a desired effect in the subject, said musical instrument comprising nine separate sound actuators each of which configured to cause the musical instrument to generate a different frequency selected from the group of frequencies comprising 174 Hz, 285 Hz, 396 Hz, 417 Hz, 528 Hz, 639 Hz, 741 Hz, 852 Hz and 963 Hz, the musical instrument being configured such that physically manipulating the sound actuators causes the musical instrument to generate the frequency corresponding to the sound actuator being manipulated.

In another aspect, the present invention provides for a device for practicing sound healing, said device configured to generate sound frequencies comprising 174 Hz, 285 Hz, 396 Hz, 417 Hz, 528 Hz, 639 Hz, 741 Hz, 852 Hz and 963 Hz.

In another aspect, the present invention provides for a musical scale comprising the following nine frequencies 174 Hz, 285 Hz, 396 Hz, 417 Hz, 528 Hz, 639 Hz, 741 Hz, 852 Hz and 963 Hz.

In another embodiment, the present invention relates to a musical instrument comprising: one or more sound bodies, each sound body including elements having dimensions that are determined using the number phi ($\phi$); and nine strings extending over a top surface of the one or more bodies, one string being tuned to vibrate at 963 Hz, another string being tuned to vibrate at 852 Hz, another string being tuned to vibrate at 741 Hz, another string being tuned to vibrate at 639 Hz, another string being tuned to vibrate at 528 Hz, another string being tuned to vibrate at 417 Hz, another string being tuned to vibrate at 396 Hz, another string being tuned to vibrate at 285 Hz and another string being tuned to vibrate at 174 Hz.

DESCRIPTION OF THE DRAWINGS

In the drawings like characters of reference indicate corresponding parts in the different figures.

DETAILED DESCRIPTION OF THE INVENTION

Figure 1:
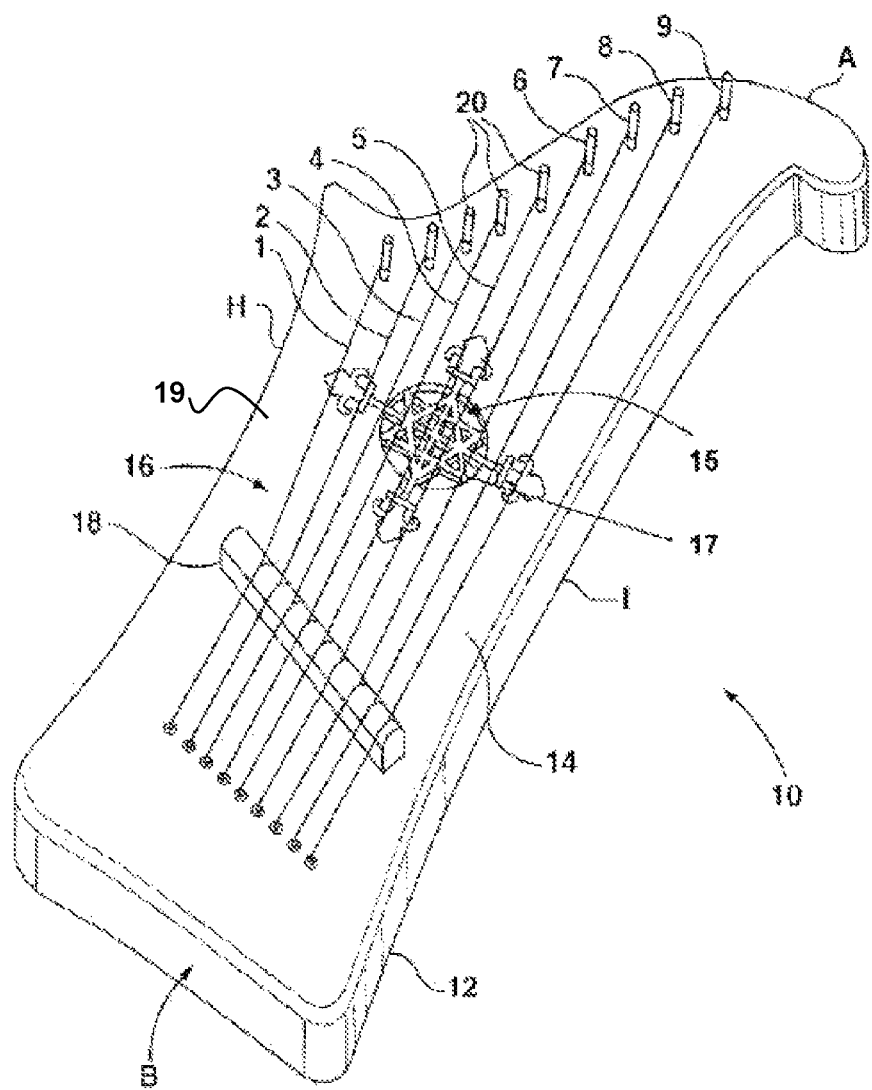
FIG. 1 is a perspective view of a musical instrument made in accordance with one embodiment of the present invention.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise.

"Music" in this document refers to an art of sound in time that expresses ideas and emotions in significant forms through the elements of rhythm, melody, harmony, and color.

Overview

In one embodiment, the present invention describes a musical instrument, which may be either acoustical or electronic. The musical instrument may include nine separate sound actuators. Each sound actuator may be configured to cause the musical instrument to generate a different frequency selected from the group of frequencies comprising 174 Hz, 285 Hz, 396 Hz, 417 Hz, 528 Hz, 639 Hz, 741 Hz, 852 Hz and 963 Hz. The musical instrument may be configured such that physically manipulating the sound actuators causes the musical instrument to generate the frequency corresponding to the sound actuator manipulated. In aspects, the musical instruments of the present invention, in either acoustic or electronic devices, may be used in methods for therapy, teaching music or healing, or in methods for creating music.

The inventor has intimate familiarity with Sound Healing. In her practice the inventor has worked with individuals having problems of the body, mind and soul. That is, with individuals having problems generally perceived as being specific to a local body area, individuals having more systemic diseases as well as with the spiritual aspect of an individual. Following treatment with musical instruments of the present invention, remarkable recoveries from body, mind and soul have been achieved.

In another embodiment, the present invention describes musical instruments having a Harmonious Scale. The Harmonious Scale is atonal and may consist essentially of 9 frequencies. In this document, the term "Atonal" means a manner of organizing tones so that no one of them may have greater importance than the others. The atonal scale of nine (9) frequencies described in this invention is referred to as the Harmonious Scale.

As previously explained, the present diatonic system of Western music consists of a tonal system in which specific notes such as the tonic, dominant and leading notes have more importance than the other notes. The Harmonious Scale being atonal may remove the tension that may normally be built up while we await the return of the tonic, which can sometimes feel like safety. The Harmonious Scale has no tonic and there are no major or minor keys or modulations to other keys, and no key signatures, no sharps, flats or accidentals. The Harmonious Scale may consist essentially of 9 precise frequencies. With the Harmonious Scale a person may start or end on any note without adhering to complex composition rules common to the diatonic system. Only certain intervals or chord combinations within the diatonic system sound pleasing. This novel Harmonious system may make music composition easier and may open up a whole new field of "creative" and "intuitive" playing for persons who find the study of Western music too difficult. A musical performer often "becomes one" or is in the "zone" with his/her instrument and without worry of adhering to complicated composition rules. Improvising, performing and sound healing may become easier with the use of the musical instruments of the present invention. Therefore, music expression and creativity may have no boundaries within the scope of people, their age, intellectual ability, race, culture and language, or nations. People from around the world, young and old, of simple or highly evolved abilities, may understand, perform, compose, improvise together in a universal simple Harmonious System where "all is one" and there is no wrong way to play. Because of its simplicity, the Harmonious Scale may also allow mastery of this Harmonious System very quickly and at a younger age.

The Harmonious Scale is based on Pythagoras and Plato's ancient Greek "MODAL" system. Pythagoras and Plato taught that all sounds have an "affect" on everything around us, so basically "You are what you listen to." For example: listening to dance rhythms would have the modal affect of inspiring others to dance. Another example would be to take the time signature out of the creative musical experience. The modal effect here is one of freedom of expansion, of intuition and consciousness, because all structure and sense of time is eliminated.

The scale of the present invention represents a system of 9 frequencies, all in harmony, with each other and with nature. The Harmonious Scale may be utilized as a new system of tuning and scale system for a new category of musical instruments which may have major implications for personal and world healing. These nine frequencies of the Harmonious Scale are 174 Hz, 285 Hz, 396 Hz, 417 Hz, 528 Hz, 639 Hz, 741 Hz, 852 Hz and 963 Hz. The nine frequencies are a mathematical set of vibrations which are so complete that if one were to try to continue the sequence the whole set would just repeat itself. That is, if one were to continue this mathematical sequence, the number following 963 would be 174 and the sequence would repeat itself over and over again.

Harmony

As stated in the Background section of this document, another definition of "harmony" surged, which may be described as a satisfying arrangement marked by even distribution of elements, as in design, proportion, and symmetry. The inventor, however, proposes in the present invention that the proportion be a Golden or Divine Proportion, the design a Divine Design and the symmetry a Divine Symmetry. The newly created definition of musical "harmony" presented herein is based on numerology and on how music may be interrelated with the ALL, the whole universe, according to Plato and Pythagoras' teachings. The new Harmonious Scale of the present invention, its tuning system, and the instruments upon which the Divine frequencies are created, may be in perfect harmony with all that we know. What was lost is now recovered in the Harmonious Scaled Instruments.

The Harmonious Scale

Pythagoras, the 6$^{th}$ century BCE mathematician, philosopher, and musical, theorist whose research gave rise to the science of Numerology, was the first person to realize that numbers may be the foundation of the universe, and music a wonderful harmonious system. During his time, it was widely accepted that the universe was created from vibrating energy, something that modern scientists might call a wavelength or electromagnetic energy. Pythagoras taught the world that numbers have the power to bring all of life into unity and harmony. Pythagoras taught that there were only 9 numbers. 1, 2, 3, 4, 5, 6, 7, 8, 9 and anything with multiple numbers could all be reduced to a single digit by adding up the individual digits that make up the number you are reducing. For example: 10=1+0=1, 11=1+1=2, 12=1+2=3. No matter how many digits a number has, it may always be reduced to a single digit, and the sequence 1 thru 9, repeats itself over and over again.

Referring to Table 1, if we consider the Harmonious Scale and add up all 3 digits horizontally, then a reoccurring pattern happens.

TABLE 1

174 = 1 + 7 + 4 = 12 = 1 + 2 = 3
285 = 2 + 8 + 5 = 15 = 1 + 5 = 6
396 = 3 + 9 + 6 = 18 = 1 + 8 = 9
417 = 4 + 1 + 7 = 12 = 1 + 2 = 3
528 = 5 + 2 + 8 = 15 = 1 + 5 = 6
639 = 6 + 3 + 9 = 18 = 1 + 8 = 9

TABLE 1-continued

741 = 7 + 4 + 1 = 12 = 1 + 2 = 3
852 = 8 + 5 + 2 = 15 = 1 + 5 = 6
963 = 9 + 6 + 3 = 18 = 1 + 8 = 9

The Harmonious Scale may also find its roots in mathematics, and it is based on 3rds, the triangle or triad. This may be representative of the Holy Trinity, common across many religions, including Christian trinity (the Father, Son, and Holy Ghost), Vedic trinities include Brahma, Vishnu and Shiva and their consorts Saraswati, Lakshmi, and Kali to name just a few. In Metaphysic study, "3" symbolizes Divine manifestation into the physical. It is representative of the triangle: the strongest geometric form from which life itself is built. John Keely, inventor of Keely Motor and discoverer of Sympathetic Vibratory Physics, expert in electromagnetic technologies wrote: "the vibrations of 3$^{rd}$, 6ths, and 9ths were extraordinarily powerful". In his experiments, he proved that settings of 3$^{rd}$, 6$^{th}$, and 9ths get the best effects. Nikola Tesla, the renowned American Inventor wrote: "If you only knew the magnificence of the 3, 6, and 9, then you would have a key to the universe" (peswiki.com/index.php/Power Pedia: John Keely).

Referring to Table 2, it is shown that most numbers of the scale of the present invention are 111 Hz apart, with 2 numbers being 21 Hz and 102 Hz apart. According to the Pythagorean Theory of Numerology, if one were to reduce all of these numbers to a single digit they would all add up to 3. Accordingly, the Harmonious Scale may also find a basis on the sum and difference of Divine Proportion.

TABLE 2

| 963 − 852 | 852 − 741 | 741 − 639 | 639 − 528 | 528 − 417 | 417 − 396 | 396 − 285 | 285 − 174 |
|---|---|---|---|---|---|---|---|
| 111 | 111 | 102 | 111 | 111 | 21 | 111 | 111 |

111 = 1 + 1 + 1 = 3
102 = 1 + 2 = 3
21 = 2 + 1 = 3

The well known Fibonacci sequence is as follows:

0, 1, 1, 2, 3, 5, 8, 13, 21, 34, 55, 89 . . . to infinity.

The first two Fibonacci numbers are 0 and 1, and each subsequent number is the sum of the previous two. The pattern is of even, odd, odd numbers, continuing the pattern of even, odd, odd, until infinity. The ratio of each successive pair of numbers in the Fibonacci series quickly converges on phi (φ), 1.6180339887 . . . , as 5 divided by 3 is 1.666, 8 divided by 5 is 1.60, 13 divided by 8 is 1.625 and so on. Fibonacci calls this ratio the Divine Proportion, or Golden Mean, or Golden Proportion, or how everything in nature is created. Drunvalo Melchizedek explains in his book, the process of creation through Sacred Geometry, using the Fibonacci Sequence and phi ratios (*The Ancient Secret of the Flower of Life*, Volume 2, Ed. Margaret Pinyan, Light Technology Publishing, 2000). On page 244, he explains how 3$^2$ is the basic unit to create the Fibonacci Spiral, which is represented by the star tetrahedron, or Star of David, two triangles overlapping, one spiralling upward into the heavens and the other spiralling down bringing the heavenly energy down to earth. This may represent bringing the Christ Consciousness into the physical.

Table 3 shows how each of the frequencies of the Harmonious Scale may be the sum of Fibonacci numbers. One may notice that all 9 frequencies of the scale of the present invention may carry the same common frequencies within their sums, therefore the nine frequencies of the present invention are harmonious with one another, and they may carry a very powerful creative spiralling energy, similar to that of nature itself.

More recently, the other 3 frequencies were used by Dr. Joseph Puleo from Idaho assisted by Dr. Leonard Harowitz, Harvard trained award winning investigator. Their research on what they call "The Original Solfeggio Scale" is docu-

TABLE 3

174 is the sum of 7 sets of Fibonacci numbers:
{1 + 8 + 21 + 144}, {1 + 3 + 5 + 21 + 144}, {1 + 8 + 21 + 55 + 89}, {1 + 3 + 5 + 8 + 13 + 144},
{1 + 3 + 5 + 21 + 55 + 89}, {1 + 3 + 5 + 9 + 13 + 55 + 89}, {1 + 3 + 5 + 8 + 13 + 21 + 34 + 89}.
285 is the sum of 9 sets of Fibonacci numbers:
{5 + 13 + 34 + 233}, {2 + 3 + 13 + 34 + 233}, {5 + 13 + 34 + 89 + 144}, {2 + 3 + 5 + 8 + 34 + 233},
{2 + 3 + 13 + 34 + 89 + 144}, {2 + 3 + 5 + 8 + 13 + 21 + 233}, {2 + 3 + 5 + 8 + 34 + 89 + 144},
{2 + 3 + 5 + 8 + 13 + 21 + 89 + 144}, {2 + 3 + 5 + 8 + 13 + 21 + 34 + 55 + 144}.
396 is the sum of 12 sets of Fibonacci numbers:
{1 + 5 + 13 + 377}, {1 + 2 + 3 + 13 + 377}, {1 + 5 + 13 + 144 + 233}, {1 + 2 + 3 + 5 + 8 + 377},
{1 + 2 + 3 + 13 + 144 + 233}, {1 + 5 + 13 + 55 + 89 + 233}, {1 + 2 + 3 + 5 + 8 + 144 + 233},
{1 + 2 + 3 + 13 + 55 + 89 + 233}, {1 + 5 + 13 + 21 + 34 + 89 + 233}, {1 + 2 + 3 + 5 + 8 + 55 + 89 + 233},
{1 + 2 + 3 + 13 + 21 + 34 + 89 + 233}, {1 + 2 + 3 + 5 + 8 + 21 + 34 + 89 + 233}.
417 is the sum of 15 sets of Fibonacci numbers:
{1 + 5 + 34 + 377}, {1 + 2 + 3 + 34 + 377}, {1 + 5 + 13 + 21 + 377}, {1 + 5 + 34 + 144 + 233},
{1 + 2 + 3 + 13 + 21 + 377}, {1 + 2 + 3 + 34 + 144 + 233}, {1 + 5 + 13 + 21 + 144 + 233},
{1 + 5 + 34 + 55 + 89 + 233}, {1 + 2 + 3 + 5 + 8 + 21 + 377}, {1 + 2 + 3 + 13 + 21 + 144 + 233},
{1 + 2 + 3 + 34 + 55 + 89 + 233}, {1 + 5 + 13 + 21 + 55 + 89 + 233}, {1 + 2 + 3 + 5 + 8 + 21 + 144 + 233},
{1 + 2 + 3 + 13 + 21 + 55 + 89 + 233}, {1 + 2 + 3 + 5 + 8 + 21 + 55 + 89 + 233}.
528 is the sum of 7 sets of Fibonacci numbers:
{2 + 5 + 144 + 377}, {2 + 5 + 55 + 89 + 377}, {2 + 5 + 21 + 34 + 89 + 377}, {2 + 5 + 55 + 89 + 144 + 233},
{2 + 5 + 8 + 13 + 34 + 89 + 377}, {2 + 5 + 21 + 34 + 89 + 144 + 233}, {2 + 5 + 8 + 13 + 34 + 89 + 144 + 233}.
639 is the sum of 20 sets of Fibonacci numbers:
{8 + 21 + 610}, {3 + 5 + 21 + 610}, {8 + 21 + 233 + 377}, {1 + 2 + 5 + 21 + 610}, {3 + 5 + 8 + 13 + 610},
{3 + 5 + 21 + 233 + 377}, {8 + 21 + 89 + 144 + 377}, {1 + 2 + 5 + 8 + 13 + 610},
{1 + 2 + 5 + 21 + 233 + 377}, {3 + 5 + 8 + 13 + 233 + 377}, {3 + 5 + 21 + 89 + 144 + 377},
{8 + 21 + 34 + 55 + 144 + 377}, {1 + 2 + 5 + 8 + 13 + 233 + 377}, {1 + 2 + 5 + 21 + 89 + 144 + 377},
{3 + 5 + 8 + 13 + 89 + 144 + 377}, {3 + 5 + 21 + 34 + 55 + 144 + 377}, {1 + 2 + 5 + 8 + 13 + 89 + 144 + 377},
{1 + 2 + 5 + 21 + 34 + 55 + 144 + 377}, {3 + 5 + 8 + 13 + 34 + 55 + 144 + 377},
{1 + 2 + 5 + 8 + 13 + 34 + 55 + 144 + 377}.
741 is the sum of 21 sets of Fibonacci numbers:
{8 + 34 + 89 + 610}, {3 + 5 + 34 + 89 + 610}, {8 + 13 + 21 + 89 + 610},
{8 + 34 + 89 + 233 + 377}, {1 + 2 + 5 + 34 + 89 + 610}, {3 + 5 + 13 + 21 + 89 + 610},
{3 + 5 + 34 + 89 + 233 + 377}, {8 + 13 + 21 + 34 + 55 + 610}, {8 + 13 + 21 + 89 + 233 + 377},
{1 + 2 + 5 + 13 + 21 + 89 + 610}, {1 + 2 + 5 + 34 + 89 + 233 + 377},
{3 + 5 + 13 + 21 + 34 + 55 + 610}, {3 + 5 + 13 + 21 + 89 + 233 + 377},
{8 + 13 + 21 + 34 + 55 + 233 + 377}, {1 + 2 + 5 + 13 + 21 + 34 + 55 + 610},
{1 + 2 + 5 + 13 + 21 + 89 + 144 + 377}, {3 + 5 + 13 + 21 + 34 + 55 + 233 + 377},
{8 + 13 + 21 + 34 + 55 + 89 + 144 + 377}, {1 + 2 + 5 + 13 + 21 + 34 + 55 + 233 + 377},
{3 + 5 + 13 + 21 + 34 + 55 + 89 + 144 + 377}, {1 + 2 + 5 + 13 + 21 + 34 + 55 + 89 + 144 + 377}.
852 is the sum of 14 sets of Fibonacci numbers:
{1 + 8 + 233 + 610}, {1 + 3 + 5 + 233 + 610}, {1 + 8 + 89 + 144 + 610},
{1 + 35 + 89 + 144 + 610}, {1 + 8 + 34 + 55 + 144 + 610}, {1 + 8 + 89 + 144 + 233 + 377},
{1 + 3 + 5 + 34 + 55 + 144 + 610}, {1 + 3 + 5 + 89 + 144 + 233 + 377},
{1 + 8 + 13 + 21 + 55 + 144 + 610}, {1 + 8 + 34 + 55 + 144 + 233 + 377},
{1 + 3 + 5 + 13 + 21 + 55 + 144 + 610}, {1 + 3 + 5 + 34 + 55 + 144 + 233 + 377},
{1 + 8 + 13 + 21 + 55 + 144 + 233 + 377}, {1 + 3 + 5 + 13 + 21 + 55 + 144 + 233 + 377}.
963 is the sum of 12 sets of Fibonacci numbers:
{2 + 8 + 21 + 89 + 233 + 610}, {2 + 3 + 5 + 21 + 89 + 233 + 610},
{2 + 8 + 21 + 34 + 55 + 233 + 610}, {2 + 3 + 5 + 8 + 13 + 89 + 233 + 610},
{2 + 3 + 5 + 21 + 34 + 55 + 233 + 610}, {2 + 8 + 21 + 34 + 55 + 89 + 144 + 610},
{2 + 3 + 5 + 8 + 13 + 34 + 55 + 233 + 610},
{2 + 3 + 5 + 21 + 34 + 55 + 89 + 144 + 610}, {2 + 8 + 21 + 34 + 55 + 89 + 144 + 233 + 377},
{2 + 3 + 5 + 8 + 13 + 34 + 55 + 89 + 144 + 610},
{2 + 3 + 5 + 21 + 34 + 55 + 89 + 144 + 233 + 377},
{2 + 3 + 5 + 8 + 13 + 34 + 55 + 89 + 144 + 233 + 377}.

Referring to Table 4, the Harmonious Scale of the present invention, may also be seen as a system of 2 tetra chords joined by 528 Hz which is the frequency used by genetic biochemists to repair broken DNA, the genetic blueprint upon which life is based.

TABLE 4

| 174 | 285 | 396 | 417 | 528 | 639 | 741 | 852 | 963 |
| --- | --- | --- | --- | --- | --- | --- | --- | --- |

Six of these nine original sound frequencies were apparently used in the great hymn to St. John the Baptist that along with many Gregorian chants, were lost centuries ago according to church officials. The chants and their special tones were believed to impart special spiritual blessings when sung in harmony.

mented in the book "Healing Codes for the Biological Apocalypse" (Tetrahedron Publishing Group, LLC, Suite 147, 206 North 4th Ave, Sandpoint, Id., USA, 83864, 2007). However, the nine frequencies have never being unified to create a new single harmonious scale, or to create new musical instruments, or for healing purposes.

Instruments of the Present Invention

Figure 2:
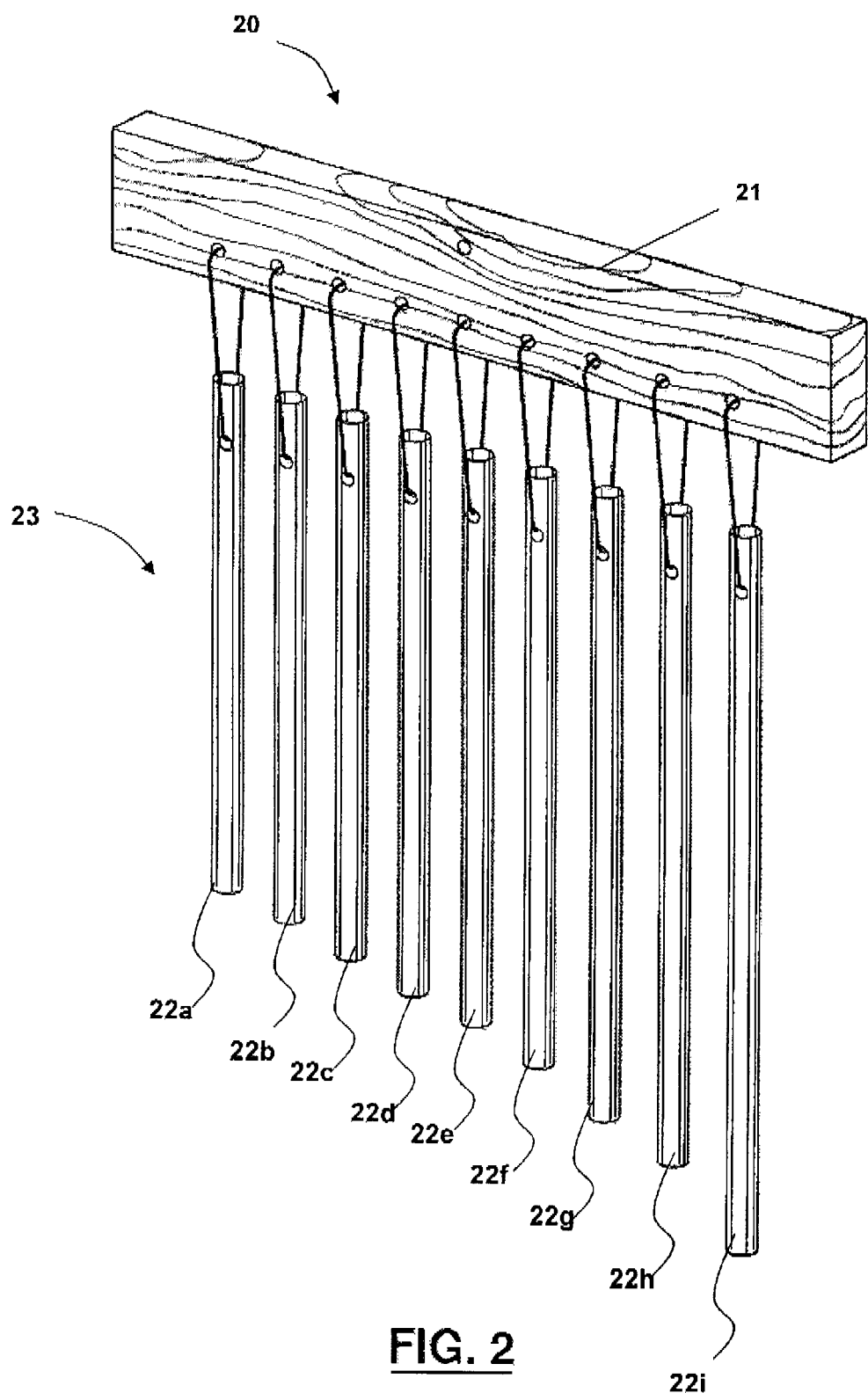
FIG. 2 is a perspective view of a musical instrument made in accordance with one embodiment of the present invention.
Figure 5:
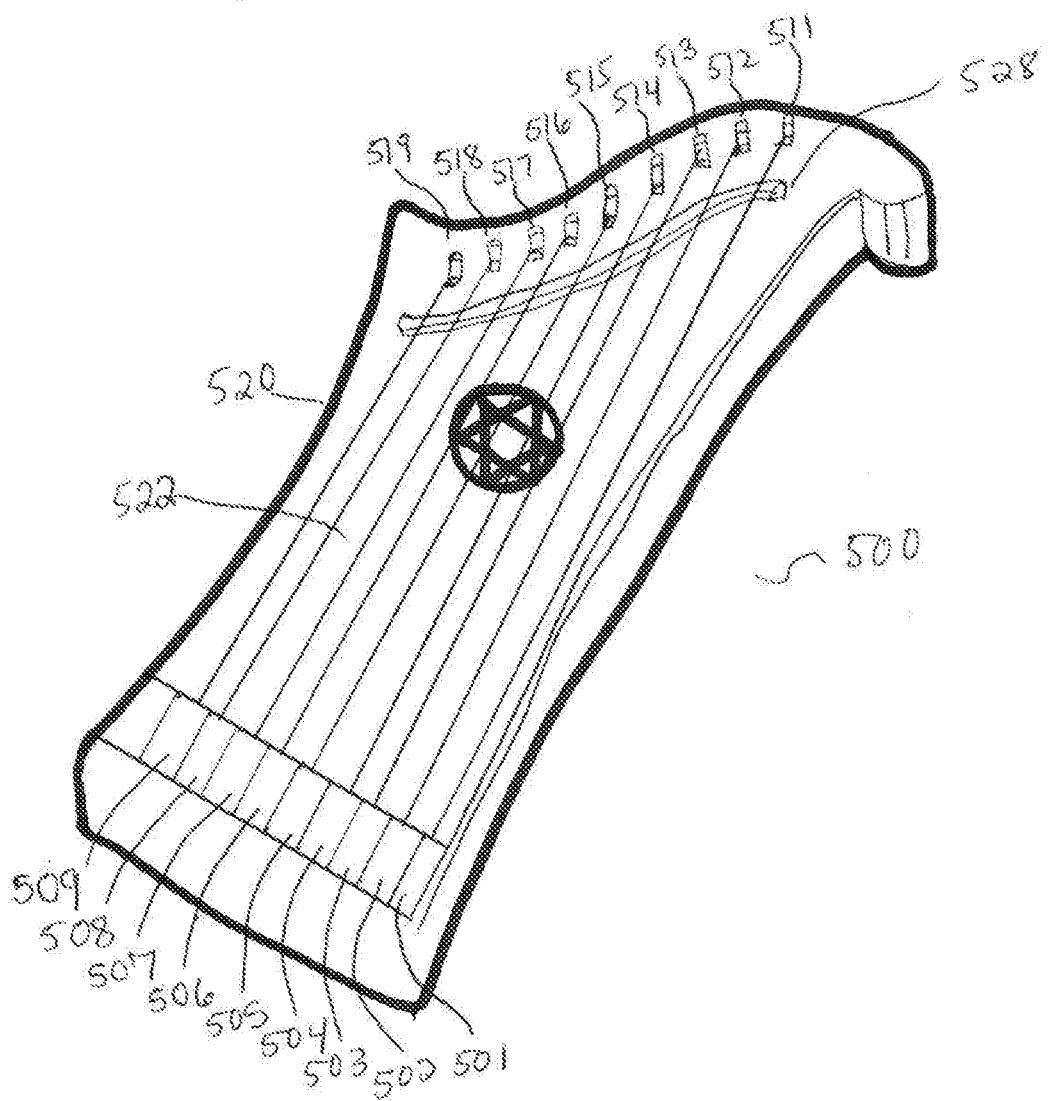
FIG. 5 is a top view of a musical instrument made in accordance with one embodiment of the present invention.

To utilize the Harmonious Scale of the present invention, a new category of instruments, which may be either acoustic or electronic, may need to be made comprising the Harmonious Tuning System of the present invention. The instruments of the present invention may be called Harmonious Instruments. As such, in one embodiment, the present invention relates to a musical instrument which includes nine separate sound actuators each of which may be configured to cause the musical instrument to generate a different frequency selected from the group of frequencies comprising 174 Hz, 285 Hz, 396 Hz, 417 H2, 528 Hz, 639 Hz, 741 Hz, 852 Hz and 963 Hz, the musical instrument being configured such that physically manipulating the sound actuators causes the musical instrument to generate the frequency corresponding to the sound actuator being manipulated. There is not much use for any more notes, as they would just be repeating the same frequencies as it already contained in the 9 frequencies. Most instruments available in the world today are set up with the diatonic scale, with the 12 tone Equal Temperament Tuning System. Retrofitting today's piano to the 9 frequency based scale of the present invention may not work easily. For example, a new instrument, the Harmonious piano or keyboard may be designed with the Harmonious Scale, having 9 keys only. The Harmonious piano may look different to the common piano because it may have only white keys and only 9 frequencies. Woodwind instruments such as the flute, piccolo, clarinet, oboe may also be configured to incorporate the Harmonious Scale and may have a whole new category of instruments. New designs of all existing instruments may be considered in this Harmonious Tuning System. FIGS. 1, 2 and 5 illustrate three examples of musical instruments according to embodiments of the present invention: the Sacred Harp (FIG. 1), the Sacred Chimes (FIG. 2) and a Sacred piano (FIG. 5).

In one embodiment of the present invention, the Harmonious devices for healing and music may all be created or designed using Divine proportions, the Golden Mean.

Typical instruments today include a sound box. In the case of stringed instruments like guitars, violins, cellos, violas and so forth, the instruments consist of a sound box or body and a neck, with strings stretching over a front plate of the body and the neck. The sound box or body usually consists of a front plate, a back plate and side walls extending from the front to the back plate. A sound chamber may be formed by the front plate, back plate and side walls. The front plate may include one or more openings to the chamber. The sound box may also be substantially solid, as in the case of electric guitars. The sound board is a thin sheet of wood or a stretched membrane over which the strings of a piano, a guitar or similar instruments are positioned to increase the sound produced. The front plate previously described is the sound board of the instrument.

The instruments of the present invention may be designed using the number phi ($\phi$), the Golden Ratio or Golden Proportion. To create the instruments of the present invention, the typical sound box or resonator found in instruments today, may be replaced with one or more bodies where the acoustics may be maximized by using Sacred Geometry, and Golden Ratio in their design. As such, the sound bodies may be called Sacred Sound Chambers. The musical instrument may include one or more sound bodies. The dimensions of each sound body or of the elements within each sound body may be determined as a function of the number phi ($\phi$). For example, the maximum length of the front plate and the width of the side walls may be determined such that the proportions between the maximum length of the front plate and the width of the side wall may approximate phi ($\phi$). Another example may be that the maximum length of a first sound body and the maximum length of a second sound body may be determined such that the proportion between the first body and the second body may approximate to the number phi ($\phi$). Another example may be that the dimensions of the one or more openings on the front plate may also be determined as a function of phi ($\phi$), for example the one or more openings may be circles having diameters which may be determined as being one or more times the number phi ($\phi$) in length.

The 9 frequencies may be implemented on any instrument, which may look like the violin, cello, viola, and so forth. This implementation may be achieved by using consistent patterns based on Golden. Proportion geometry for the graduation of the top and back plates of the one or more body portions or Sacred Sound Chamber of the instrument. The use of the Golden Proportion in all instruments may allow for uniformity of the flexing of the plates, as well as optimize velocity of vibrations throughout the top and back plates of the Sacred Sound Chambers. As the density and tuning of the plates may always be taken into account, the whole pattern of the one or more bodies may be made geometrically thinner or thicker accordingly.

The arch height of the instruments of the present invention may also be based on aspects of the Golden Proportion. For example, the ideal arch height of a violin may be 16 mm.

A bridge may be defined as a device for supporting the strings on a stringed instrument and transmitting the vibration of those strings to some other structural component of the instrument, such as the sound box, in order to transfer the sound to the surrounding air. In the instruments of the present invention, the bridge position may be located in the same proportion to the one or more bodies of the instrument as the naval is to the human body, all in Golden Proportion.

Creating musical instruments, healing devices, and so forth with the Golden Proportion throughout its construction may acoustically bring about the most powerful and vibrational Sacred Sound possible. All Harmonious Scaled instruments and healing devices may have "Sacred Sound Chambers", with "Sacred Sound Holes" through which all vibrations will be emitted. All instruments may be created with Sacred Geometry in mind, and numerology, so all may be in Golden Proportion.

It will be appreciated by a person of ordinary skill in the art that the harmonious scale may be incorporated into any musical instrument, including (i) stringed instruments such as violin, viola, cello, harp, lute, banjo, guitar, bass (either in acoustic or electronic form); (ii) keyboard instruments such as pianos (including upright and grand piano), harpsichords, accordion, harmonium, organs, synthesizers; (iii) percussion instruments such as chimes, bells, triangles, xylophones, drums, bongos; (iv) wood winds and brass instruments which may use holes or valves as sound actuators which, when depressed (or covered) may cause the instrument to generate notes from the harmonious scale including flute, piccolo, clarinet, bagpipes, oboes, saxophones, bassoon, trumpet, trombones, horns, tubas, euphoniums, are all within the scope of the present invention. A percussion instrument may be any object which produces a sound when hit with an implement, shaken, rubbed, scraped, or by any other action which sets the object into vibration. A person of ordinary skill in the art would appreciate that percussion instruments such as xylophones and chimes may be configured to incorporate in its body 9 bars or sounding chimes, each bar or sounding chime when struck would produce each of the 9 frequencies of the present invention (see FIG. 2). A person of ordinary skill in the art would also appreciate that in the case of percussion instruments having membranes such as drums, nine different drums may be manufactured such that each drum may be configured to produce each of the nine frequencies of the present invention when hit.

Methods of Creating Music

The Harmonious Scale is atonal, meaning all frequencies are equal in importance, and there is no tonal center. All 9 frequencies are harmonious with each of the other frequencies of the Harmonious Scale. Therefore, using an instrument made in accordance with this invention, a composer, performer, Sound Healer or anyone else using an instrument or device designed with this set of 9 frequencies may begin and end on any one of the 9 notes without a key signature, or a set of rules defining appropriate composition, harmonious intervals or chords as all will sound good together, one note at a time, or several and the combinations have no limits. For the first time, improvisation may be totally free, and there is no wrong way to perform.

Methods of Healing

In one embodiment, the present invention provides for a method for treating a disorder in a subject. The disorder may be selected from physiological, neurological, behavioural and spiritual disorders. The method may comprise exposing a subject to one or more of the nine frequencies of the Harmonious Scale for a time effective to produce a desired effect in the subject. The nine frequencies may be produced by a musical instrument according to an embodiment of the present invention. In aspects the present invention provides for a method for treating pain, anxiety, learning, epilepsy and depression in a subject by exposing the subject to the nine frequencies of the Harmonious Scale.

In another embodiment, the present invention provides for a method for practicing sound healing. The method for practicing sound healing may comprise exposing a subject to frequencies produced by a musical instrument of the present invention for a time effective to produce a desired effect in the subject.

Healing by sound frequencies may be based on resonant entrainment of oscillating systems. This is a well-understood principle within the physical sciences and Sound Healing. For example, if a tuning fork designed to produce a frequency of 440 Hz is struck (causing it to oscillate) and then brought into the vicinity of another 440 Hz tuning fork, the second tuning fork will begin to oscillate. The first tuning fork may be said to have entrained the second or caused it to resonate. Tuning forks of a different frequency will not be affected as there is no resonance. This is considered "free resonance". "Forced resonance" occurs when one vibrating source produces vibrations in another object even though those two objects may not share the exact same frequency. The vibrations of one may entrain or change those of the other. Those vibrating sources that may be subject to the influence of "forced resonance" will resonate with many different frequencies. The physics of entrainment apply to bio-systems as well. The human body also resonates in this manner, responding to all the frequencies around it.

In Sound Healing, by the use of a musical instrument configured to incorporate the Harmonious Scale of the present invention, the concept of resonant frequency healing applies, in which the natural vibrations may be restored. Through restoring the body's own resonant frequencies and balancing its energy systems, the body may begin to heal itself. Very simply put, if a part of the body vibrates "out of harmony", a trained Sound Healer may, by use of the correct resonant frequency, entrain that part of the physical, emotional, mental, or spiritual bodies within a person's whole etheric and physical body back into "harmony" allowing for the natural healing process innate within the body to take place. This may represent a more holistic method of healing which may be capable of healing not only mind and body, but also spiritual healing.

The electrochemical activity of the nervous system, including the brain, results in the production of electromagnetic wave forms which may be objectively measured with sensitive equipment. Brain waves change frequencies based on neural activity within the brain. Because neural activity is electrochemical, brain function may be modified through the introduction of specific chemicals (drugs as prescribed by Western Medicine), by altering the brain's electromagnetic environment through induction, or through resonant entrainment techniques of Sound Healing. There are no deleterious side effects when using resonant entrainment techniques.

In Sound Healing, sonic "entrainment" occurs in which the brain waves of the listener lock into resonance with the frequencies sounded by the Sound Healer for the time of the treatment. Environmental sounds, such as birds chirping, rain, or the sound of waves, etc. may be among the most soothing on the planet, and are often used by therapists, such as for massage, reiki, cranial sacral etc. With sonic entrainment, our hearts may start to beat with the beats of the earth, and we may be "in harmony" with the universe. It is well known that the sounds of traffic, sirens, and other busy city sounds affect us as well but usually in a more negative way. We may not be able to avoid big cities and the noise, but we may drive along listening to music produced with the Harmonious Scale to help keep our energy systems balanced rather than the music that is produced with the present diatonic scale and 12 tone equal temperament system, which has been proven to be out of harmony with nature and with the human body.

In yet another embodiment, the present invention provides for a device for practicing sound healing, said device configured to generate sound frequencies comprising 174 Hz, 285 Hz, 396 Hz, 417 Hz, 528 Hz, 639 Hz, 741 Hz, 852 Hz and 963 Hz.

The use of electromagnetic frequency devices is widely used throughout Western Medicine, for diagnosis and treatment purposes. Here are just a few of the electrical frequency instruments in present therapeutic medical use today. Muscle stimulators which relieve pain, reduce spasms and edema, tonify weak muscles and assist the healing process, run at from 1 to 130 Hz. The TENS machine, used to block pain runs at about 80-100 Hz. Interferential Therapy units, which are a type of muscle stimulator runs at 3000 to 4000 Hz. Biofeedback instruments used to modify behaviours and retrain the nervous and muscular systems, run from below 1 Hz to 40 Hz. Bone growth Stimulators, used to heal broken bones run at frequencies from about 40 to 80 Hz.

The 9 frequencies of the Harmonious healing device of the present invention may be used to improve and simplify technologies used today in this field.

The middle frequency of the Harmonious Scale is 528 Hz. As previously stated, biochemists use this frequency for DNA repair. To sound healers and musicians 528 Hz is regarded as the heart of the entire electromagnetic spectrum of sound and light.

Harmonious Music Notation

Figure 3:
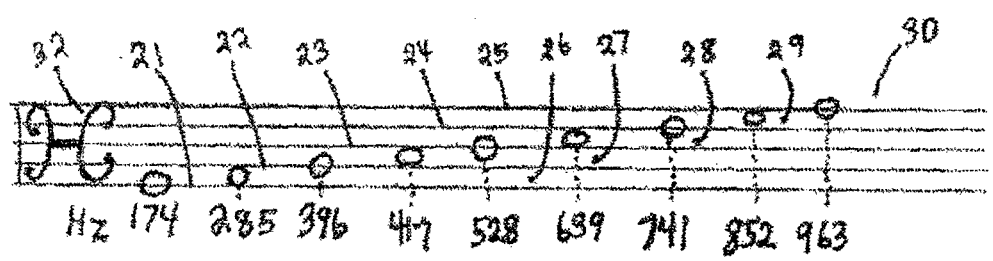
FIG. 3 is a schematic view of a notation system for writing music in accordance with one embodiment of the present invention.

Implementing the Harmonious Scale in written music may be done with the following method as illustrated in FIG. 3. Using today's manuscript paper, the Harmonious Scale of 9 frequencies may easily fit on a staff 30 of five lines (lines 21, 22, 23, 24 and 25) and four spaces (26, 27, 28 and 29) using every line and space. The pitch may be shown by placement of notes on the staff and duration may be shown with different note values and additional symbols such as dots and ties, basically utilizing the same notes that are already used in the study of music, such as quarter notes, half notes whole notes etc. and their corresponding rests.

The lines and spaces in staff 30 may indicate the frequencies the placed notes have. Line 21 (the lowermost line) may indicate a first note with a frequency of 174 Hz. Space 26 immediately above the first line may indicate a second note with a frequency of 285 Hz. Second line 22 may indicate a third note with a frequency of 396 Hz. Space 27 immediately above the second line may indicate a fourth note with a frequency of 417 Hz. Third line 23 may indicate a fifth note with a frequency of 528 Hz. Space 28 immediately above the third line may indicate a sixth note with a frequency of 639 Hz. Fourth line 24 may indicate a seventh note with a frequency of 741 Hz. Space 29 immediately above the fourth line may indicate an eighth note with a frequency of 852 Hz. Fifth line 25, being the topmost line, may indicate the highest ninth note with a frequency of 963 Hz.

A staff of written music generally begins with a clef and the Harmonious Clef 32 is demonstrated in FIG. 3 utilizing an H with the 528 Hz line crossed with the middle of the H. Following the clef may or may not be a time signature depending on the nature of the piece. In the case of a time signature, measures or bar lines will divide the piece into regular groupings of beats, according to the time signatures specification. A piece may change time signatures during the piece by indicating a new time signature, and any bars following, would be in the new time. Directions to the player regarding matters such as tempo and dynamics or mode may be added above or below the staff. For vocal music, lyrics may be written in with the words or sounds under the corresponding notes.

Figure 4:
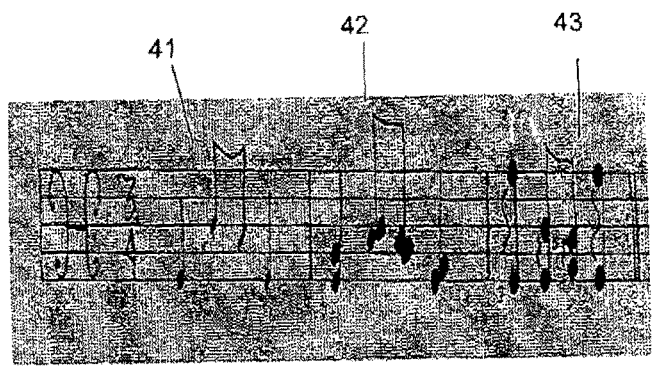
FIG. 4 is a schematic view of a short piece of music written using the notation system illustrated in FIG. 3.

FIG. 4 illustrates how rhythms and time signatures may be used, single notes are shown in the first bar 41, clusters in the second bar 42 and strumming of all the notes is indicated in the third bar 43. Notation for ensembles and orchestras is a score showing music for all players together, while parts contain only the music played by an individual musician.

An Example of the Harmonious Scale System in Music Education and Sound Healing

The following may be used as a guideline for teaching others how to use instruments or devices with the Harmonious Scale and Tuning System of the present invention.

(1) Align yourself with your heart, come into a space of love, state a prayer of intention: Decide as an individual or as a group, the purpose behind the sound, what is it you are trying to create or heal. This intention is very important as the energy, or your purpose is transmitted through the sound. Use positive words and affirm your words in the present tense, For example: "We live in peace"; "we live in joy"; "we live in harmony and love"; "I am healed on all levels"; "you are totally balanced and in good health"; "the waters of the earth are clean and pure, a perfect ecosystem". With the use of your 5 senses, and emotions, visualize, taste, smell, hear and feel what this intention looks like, feels like, tastes and smells and sounds like, affirming that it is done.

If it is your custom to ask for higher guidance and assistance in fulfilling this intention, the philosophy of this practice recognizes "ALL IS ONE", therefore there is no dogma and it is not a religion. Everyone around the world, regardless of religious affiliation or faith can join together for a common purpose.

(2) Align yourself totally and become "one" with the instrument. Whether an individual, instrumentalist or orchestra is reading music or improvising, it does not matter. Each musician will learn to get in the "zone" or become "one" with the instrument, allowing the music to flow through them, allowing the breath to be the vehicle through which the sound moves. This is a meditative state in which higher levels of intuition and higher guidance can be accessed.

(3) Offer gratitude that your intention is fulfilled.

As with anything in life, the more energy we put into our projects, and the more people working on the same goal, the closer we come to fulfilling each dream, and all is possible. Sound Healers and other Energy Medicine Practitioners know that one session can produce the results in some instances; some others take 2 or 3 or maybe 10 or more. This methodology recognizes that the only limitations we have are those that we impose upon ourselves and others. Within school education systems, this methodology system will teach children to align, themselves with a purpose and to live intentionally. It teaches children the original powerful purpose of sound and music and how they can make a difference in the world, it reminds us all to think before we speak, before we produce the sounds and vibrations we put out into the world which will have an affect on everything else. This methodology reminds us of our true soul purpose to make a difference in the world (hopefully for the better), to find that power and to live and practice it. Within the medical/healing systems, this methodology will teach practitioners to align themselves completely with their job, as their intention to heal, and from a place of love must be present. It will simplify the technology used for treating illnesses and economically be more advantageous. It will heal on all levels of our being: body-mind and soul rather than just body-mind. It will heal more deeply and completely, therefore reoccurrences of disease and illnesses are less likely, and the speed of recovery will be profound, which allows people to get on with living, and practitioners free to help others. This may dramatically help health care systems.

Disclosed herein is a new category of musical instruments or devices which may be used in methods for tuning, teaching, therapy and healing. The Sacred Harp and Sacred Chime described in the Examples provided below, are two examples of instruments constructed with the Harmonious Scale and Tuning System and they may be used in Sound Healing. The methodology in using this Harmonious Tuning system may enable us to teach and promote awareness of intentional use of our sounds and music through the understanding and teaching of physics of vibration, resonance vibrations theory and vibrational entrainment. Through this understanding of how powerful vibrations are, we may all make a difference affecting the health and wellness of ourselves, our families, our communities and the world. The methodologies of the present invention may promote creativity, intuition, meditation, sacred sound and healing and unity among all people, regardless of age, race, religion or anything else that has in the past, kept us divided. This atonal Harmonious Scale and Tuning System may be a reflection of the sounds that will unite the world in peace, joy, love and harmony.

The above disclosure generally describes the present invention. A more complete understanding can be obtained by reference to the following specific Examples. These Examples are described solely for purposes of illustration and are not intended to limit the scope of the invention Changes in form and substitution of equivalents are contemplated as circumstances may suggest or render expedient. Although specific terms have been employed herein, such terms are intended in a descriptive sense and not for purposes of limitation.

EXAMPLES

The Sacred Harp

FIG. 1 shows a musical instrument incorporating the Harmonious Scale in accordance to one embodiment of the present invention. The harp depicted in FIG. 1, which may be referred to as the Sacred Harp, may include a body portion 12, which may be made of a hard wood such as cherry, for better resonance. The resonator or sound box 14 may be formed in the body portion 12 and it may be hollow so as to maximize the sound generated by nine (1-9) strings 16 mounted adjacent thereto, over the front plate or sound board 19 of the instrument. Strings 16 may essentially be similar to standard guitar or harp strings. Each of the strings may be of different length. The Harmonious Harp of FIG. 1 may include dimensions from point A to point B of about 68 cm and may be about 16.25 cm from point H to point I. A person of ordinary skill in the art would understand that other dimensions are possible so long as the 9 strings 1-9 generate the 9 frequencies of the present invention. There may be a sound hole 15 on the front 19 hand-carved, which may have 9 cm (3 cm radius). Any suitable decorative feature, such as the Star of David 17, or 2 triangles overlapped, one pointing up and the other pointing down, may be added. The strings 1-9 may feed in through the back of the instrument each through a separate entry. The strings 1-9 may be held by a traditional knot inside the sound box 14 and thread through the front of the sound box 14, each through their corresponding holes where the string may be pulled tight across a wooden bridge 18 and then across the length of the sound box 14 and secured to tuning pins 20.

In one embodiment, the harmonious harp of the present invention may include 9 strings, each string may be configured to vibrate at a different harmonious frequency of the Harmonious Scale. The frequency generated by each string may be a function of the strings length, gauge and the tension applied to the string Strings 1 through 9 may get progressively longer, and their thicknesses (gauge) as well as the tension applied to them may be selected so that together the strings produce all of the notes (frequencies) of the harmonious scale of the present invention. The highest tone (frequency) may be generated by the shortest string, string 1. String 1 may preferably have a gauge of 0.012 and may be tensioned sufficiently to generate a frequency of 963 Hz when plucked or strummed. String 2 may preferably be longer and may be thicker that string 1 having a gauge of 0.014. String 2 may be tensioned to vibrate at a frequency of 852 Hz. String 3 may preferably have a gauge of 0.015 and may be tensioned to vibrate at 741 Hz. String 4 may have a gauge of 0.018 and may be tensioned to vibrate at 639 Hz. String 5 may have a gauge of 0.018 and may be tensioned to vibrate at 528 Hz. String 6 may have a gauge of 0.018 and may be tensioned to vibrate at 417 Hz. String 7 may have a gauge of 0.020 and may be tensioned to vibrate at 396 Hz. String 8 may have a gauge of 0.020 and may be tensioned to vibrate at 285 Hz. Finally, string 9, which may be the longest string and may preferably have a gauge of 0.20 and may be tensioned sufficiently to vibrate at 174 Hz.

With continued reference to FIG. 1, the harp 10 is an acoustic instrument which may be plucked or strummed. It may be held with the base (B) in one's lap if sitting or in one's arms if standing and held upright and slanted slightly to the left with the sound hole facing away from the performer. Strings 1 through 9 may act as sound actuators which, when physically manipulated by a user, such as by plucking or strumming, may cause the harp to generate the frequencies associated with the strings. The strings, each being coupled to the resonator (sound box), may transfer their vibrations to the resonator, which permit the musical instrument to generate audible musical tones even when the strings are manipulated gently.

The calming and healing properties of the Harmonious Scale may be particularly effective when the instrument tuned to it takes the form of a harp, as the musical properties of music emanating from a harp are generally more relaxing and more calming than other instruments. The harp may therefore be well suited to the harmonious scale and in particular for use in sound/music therapy.

The Sacred Chime

FIG. 2 shows a musical instrument incorporating the Harmonious Scale in accordance to another embodiment of the present invention. The chime depicted in FIG. 2, which may be referred to as the Sacred Chime, may include elongated suspender 21, which may be in the form of a rod, from which nine (22a-22i) of sounding bodies or chime bells 23 are suspended and dangle at a distance from each other. Sounding bodies 23 may made substantially tubular or in other shapes. Bodies 23 may be made of materials such as metal, wood, glass, bamboo, shell, stone or porcelain. The shape, material, thickness, hanging method of the sounding bodies 23 may have a large impact on the sound each body 22a-22i produces.

Each of the 9 bodies 22a-22i of the Sacred Chime is designed to produce one of the nine frequencies of the Harmonious Scale, such that when struck, each body 22a-22i of the Sacred Chime produces each of the 9 frequencies of the present invention.

FIG. 5 shows a stringed keyboard 500 incorporating the Harmonious Scale in accordance to one embodiment of the present invention. The stringed keyboard 500 depicted in FIG. 5 may include a body portion 520, which may be made of a hard wood such as cherry, for better resonance, nine strings 511-519 mounted over a front plate or sound board 522 of the stringed keyboard 500 and across a bridge 528, and nine keys 501-509. Each key 501-509 being associated with a corresponding string 511-519. Each of the strings 511-519 may be of different length. Each string 511-519 may be configured to vibrate at a different harmonious frequency of the Harmonious Scale. String 511 generates a frequency of 174 Hz when struck by key 501. String 512 generates frequency of 285 Hz when struck by key 502. String 513 generates frequency 396 Hz when struck by key 503. String 514 generates frequency 417 Hz when struck by key 504. String 515 generates frequency 528 Hz when struck by key 505. String 516 generates frequency 639 Hz when struck by key 506. String 517 generates frequency 741 Hz when struck by key 507. String 518 generates frequency 852 Hz when struck by key 508. Finally, string 519 generates frequency 963 Hz when struck by key 509.

A specific embodiment of the present invention has been disclosed; however, several variations of the disclosed embodiment could be envisioned as within the scope of this invention. It is to be understood that the present invention is not limited to the embodiments described above, but encompasses any and all embodiments within the scope of the following claims.

I claim:

1. A method for treating a disorder in a subject comprising exposing the subject to nine atonal sound frequencies, said nine atonal sound frequencies selected from the group consisting of: 174 Hz, 285 Hz, 396 Hz, 417 Hz, 528 Hz, 639 Hz, 741 Hz, 852 Hz and 963 Hz, the nine atonal sound frequencies produced by an acoustic musical instrument, wherein the acoustic musical instrument comprises a sound board having exactly nine separate sound actuators each of which configured to cause the musical instrument to generate each one of the nine atonal sound frequencies, the musical instrument being configured such that physically manipulating the sound actuators causes the musical instrument to generate the sound frequency corresponding to the sound actuator being manipulated, and wherein the disorder is selected from the group consisting of pain, stress, anxiety, learning, epilepsy and depression, wherein the acoustic musical instrument is a keyboard instrument having strings or a stringed instrument.

2. The method of claim 1, wherein said disorder is pain.

3. The method of claim 1, wherein the musical instrument is a keyboard instrument having strings.

4. The method of claim 1, wherein the disorder is epilepsy.

5. The method of claim 1, wherein the disorder is stress.

6. The method of claim 1, wherein the disorder is anxiety.

7. The method of claim 1, wherein the disorder is learning.

8. The method of claim 1, wherein the disorder is depression.

9. The method of claim 1, wherein the acoustic musical instrument is a stringed instrument.

10. A method for healing with music, said method comprising exposing a subject to music created with frequencies produced by an acoustic musical instrument for a time effective to produce a desired effect in the subject, said musical instrument consisting of one body comprising a sound board having exactly nine separate sound actuators each of which configured to cause the musical instrument to generate a different atonal sound frequency selected from the group of frequencies consisting of 174 Hz, 285 Hz, 396 Hz, 417 Hz, 528 Hz, 639 Hz, 741 Hz, 852 Hz and 963 Hz, the musical instrument being configured such that physically manipulating the sound actuators causes the musical instrument to generate the frequency corresponding to the sound actuator being manipulated wherein the acoustic musical instrument is a keyboard instrument having strings or a stringed instrument.

11. The method of claim 10, wherein the acoustic musical instrument is a keyboard instrument having strings.

12. The method of claim 10, wherein the acoustic musical instrument is a stringed instrument.

* * * * *